United States Patent [19]
Geisen

[11] Patent Number: 6,156,755
[45] Date of Patent: Dec. 5, 2000

[54] USE OF PYRIMIDINE DERIVATIVES FOR THE PREVENTION OF CANCER, ON THEIR OWN OR IN COMBINATION WITH OTHER THERAPEUTIC MEASURES

[75] Inventor: Karl Geisen, Frankfurt, Germany

[73] Assignee: Aventis Pharma Deutschland GmbH, Frankfurt, Germany

[21] Appl. No.: 09/038,156

[22] Filed: Mar. 11, 1998

[30] Foreign Application Priority Data

Mar. 13, 1997 [DE] Germany ............................ 197 10 435

[51] Int. Cl.⁷ .................................................. A61K 31/505
[52] U.S. Cl. .......................... 514/256; 514/269; 514/272; 514/275
[58] Field of Search ..................... 514/256, 269, 514/272, 275

[56] References Cited

U.S. PATENT DOCUMENTS 5,138,058   8/1992   Geisen et al. ............................ 514/255
5,215,990   6/1993   Geisen et al. ............................ 514/255

FOREIGN PATENT DOCUMENTS

94/07867   4/1994   WIPO .

OTHER PUBLICATIONS

K. Geisen et al.; "Sorbitol –accumulating Pyrimidine Derivatives" Arzneimittel–Forsch./Drug Res. 44 (II), (1994), 1032–1043.

*Primary Examiner*—Jerome D. Goldberg
*Attorney, Agent, or Firm*—Finnegan, Henderson, Farabow, Garrett & Dunner, L.L.P

[57] ABSTRACT

Use of pyrimidine derivatives for the prevention of cancer, on their own or in combination with other therapeutic measures.

The present invention is concerned with the use of pyrimidine derivatives as agents for the prevention of carcinomatous disorders.

The pyrimidine derivatives used are active compounds of the formula I

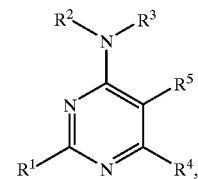

in which $R^1$ to $R^7$ have the meaning indicated, and their physiologically tolerable salts.

5 Claims, No Drawings

USE OF PYRIMIDINE DERIVATIVES FOR THE PREVENTION OF CANCER, ON THEIR OWN OR IN COMBINATION WITH OTHER THERAPEUTIC MEASURES

DESCRIPTION

Use of pyrimidine derivatives for the prevention of cancer, on their own or in combination with other therapeutic measures The present invention is concerned with the use of pyrimidine derivatives as agents for the prevention of carcinomatous disorders.

The pyrimidine derivatives used are active compounds of the formula I

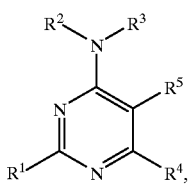

in which $R^1$ is hydrogen, halogen, cyano, nitro, trifluoromethyl, amino, ($C_1$–$C_6$)-alkyl, ($C_1$–$C_6$)-hydroxyalkyl, ($C_1$–$C_6$)-alkoxy, ($C_6$–$C_{12}$)-aryl, ($C_1$ $C_6$)-alkoxycarbonyl-($C_1$–$C_6$)-alkyl, ($C_1$–$C_6$)-alkyl-S—($C_1$–$C_6$)-alkyl, ($C_1$–$C_6$)-alkyl-SO-($C_1$–$C_6$)-alkyl, ($C_1$–$C_6$)-alkyl-SO$_2$—($C_1$–$C_6$)-alkyl, dihydroxy-($C_1$–$C_6$)-alkyl, aryl, heteroaryl, heteroaryl-($C_1$–$C_6$)-alkyl, aryl-($C_1$–$C_6$)-alkyl, ($C_1$–$C_6$)-alkoxycarbonylaryl, aryl-($C_1$–$C_6$)-alkyloxy or heteroaryl-($C_1$–$C_6$)-alkyloxy, heteroaryl is pyridyl, furyl, tetrahydrofuryl, thienyl, imidazolyl, pyrazolyl, triazolyl, thiazolyl, oxazolyl, benzothiazolyl;

where aryl and heteroaryl independently of one another can be substituted by one or more substituents selected from the group consisting of chlorine, bromine, ($C_1$–$C_6$)-alkyl, ($C_1$–$C_6$)-alkoxy, —S—($C_1$–$C_6$)-alkyl, —SO—($C_1$–$C_6$)-alkyl,—SO$_2$—($C_1$–$C_6$)-alkyl, hydroxy-($C_1$–$C_6$)-alkyl, trifluoromethyl, or

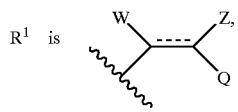 in which the dashed line is an optional double bond;

W, Q, Z independently of one another are H, ($C_1$–$C_6$)-alkyl, trifluoromethyl, phenyl, furyl, triazolyl, thiazolyl, thienyl, where phenyl, furyl, triazolyl, thiazolyl, thienyl independently of one another can be mono- to trisubstituted by ($C_1$–$C_6$)-alkyl, ($C_1$–$C_6$)-alkoxy, trifluoromethyl, hydroxyl, or $R^1$ is —(C=O)—$R^6$ $R^6$ is H, ($C_{1-6}$)-alkyl, aryl, heteroaryl heteroaryl is pyridyl, furyl, tetrahydrofuryl, thienyl, imidazolyl, pyrazolyl, triazolyl, thiazolyl, oxazolyl, benzothiazolyl; where aryl and heteroaryl independently of one another can be substituted by one to three substituents selected from the group consisting of chlorine, bromine, nitro, trifluoromethyl, ($C_{1-6}$)-alkoxy, —S—($C_1$–$C_6$)-alkyl, —SO—($C_1$–$C_6$)-alkyl, —SO$_2$—($C_1$–$C_6$)-alkyl, or $R^1$ is 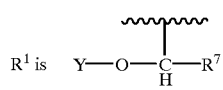

$R^7$ is aryl, heteroaryl heteroaryl is pyridyl, furyl, thienyl, imidazolyl, pyrazolyl, triazolyl, thiazolyl, oxazolyl, benzothiazolyl, benzofuranyl, benzothienyl, quinolyl, where aryl and heteroaryl independently of one another can be substituted by one to three substituents selected from the group consisting of chlorine, bromine, nitro, trifluoromethyl, ($C_1$–$C_6$)-alkyl, ($C_1$–$C_6$)-alkoxy, —S—($C_1$–$C_6$)-alkyl, —SO—($C_1$–$C_6$)-alkyl, —SO$_2$—($C_{1-6}$)-alkyl;

Y hydrogen, benzyl, acetyl, benzoyl, phenyl, naphthyl, furyl, thienyl, thiazolyl, oxazolyl, where the cycles or heterocycles can be substituted by one or two substituents selected from the group consisting of chlorine, bromine, nitro, trifluoromethyl, ($C_{1-6}$)-alkyl, ($C_1$–$C_6$)-alkoxy, —S—($C_1$–$C_6$)-alkyl, —SO—($C_1$–$C_6$)-alkyl, —SO$_2$—($C_{1-6}$)-Alkyl;

$R^2$, $R^3$ independently of one another are hydrogen, ($C_1$–$C_6$)-alkyl, ($C_6$–$C_{12}$)-aryl, ($C_6$–$C_{12}$)-arylalkyl having 1–4 alkyl carbon atoms, where aryl can be substituted by one to three substituents selected from the group consisting of chlorine, bromine, trifluoromethyl, ($C_1$–$C_6$)-alkyl, ($C_1$–$C_6$)-alkoxy, or $R^2$ and $R^3$, together with the nitrogen to which they are bonded, form the azetidino, pyrrolidino, piperidino, piperazino or morpholino group, where the heterocycles can be substituted by one or two substituents selected from the group consisting of chlorine, bromine, trifluoromethyl, ($C_1$–$C_6$)-alkyl, ($C_1$–$C_6$)-alkoxy, —S—($C_1$–$C_6$)-alkyl, —SO—($C_{1-6}$)-alkyl, —SO$_2$—($C_1$–$C_6$)-alkyl, sulfamoyl, N—($C_1$–$C_4$)-alkylsulfamoyl, N,N—($C_1$–$C_4$)-dialkylsulfamoyl, ($C_{1-6}$)-alkoxycarbonyl, N,N—($C_1$–$C_4$)-dialkylcarbamoyl, N—($C_1$–$C_4$)-alkylcarbamoyl, N—($C_6$–$C_{12}$)-arylcarbamoyl, ($C_6$–$C_{12}$)-arylcarbamoyl substituted in the aryl radical by ($C_1$–$C_4$)-alkyl, ($C_1$–$C_4$)-alkoxy, halogen, NO$_2$, NH$_2$, CN or CF$_3$, ($C_6$–$C_{12}$)-arylcarbonyl substituted in the aryl radical by ($C_1$–$C_4$)-alkoxy, halogen, NO$_2$, NH$_2$, CN or CF$_3$, ($C_1$–$C_6$)-alkylsulfonyl, ($C_1$–$C_6$)-alkylsulfinyl, ($C_6$–$C_{12}$)-arylsulfonyl, ($C_6$–$C_{12}$)-arylsulfonyl substituted in the aryl radical by ($C_{1-4}$)-alkyl, ($C_1$–$C_4$)-alkoxy, halogen, NO$_2$, NH$_2$, CN or CF$_3$, heteroarylcarbonyl or heteroarylsulfonyl;

$R^4$ and $R^5$ independently of one another are hydrogen, halogen, cyano, nitro, trifluoromethyl, amino, ($C_1$–$C_6$)-alkyl, ($C_{1-6}$)-hydroxyalkyl, ($C_1$–$C_6$)-alkoxy, ($C_6$–$C_{12}$)-aryl, naphthyl, furyl, where ($C_6$–$C_{12}$)-aryl, naphthyl and furyl can be substituted by one or two substituents selected from the group consisting of chlorine, bromine, trifluoromethyl, ($C_1$–$C_6$)-alkyl, ($C_1$–$C_6$)-alkoxy, —S—($C_1$–$C_6$)-alkyl, —SO—($C_1$–$C_6$)-alkyl, —SO$_2$—($C_{1-6}$)-alkyl, hydroxyl; and their physiologically tolerable salts.

Preferred compounds of the formula I are those in which $R^1$ is cyano, trifluoromethyl, ($C_1$–$C_6$)-alkyl, ($C_1$–$C_6$)-hydroxyalkyl, ($C_1$–$C_6$)-alkoxy or ($C_6$–$C_{12}$)-aryl;

$R^4$ and $R^5$ are hydrogen, halogen or trifluoromethyl;

$R^2$, $R^3$ independently of one another are hydrogen, ($C_1$–$C_6$)-alkyl, ($C_6$–$C_{12}$)-aryl or ($C_6$–$C_{12}$)-arylalkyl having 1–4 alkyl carbon atoms, or $R^2$ and $R^3$, together with the nitrogen to which they are bonded, form the azetidino, pyrrolidino, piperidino, piperazino or morpholino group, or an azetidino, pyrrolidino, piperidino, piperazino or morpholino group substituted by identical or different groups $R^6$ and $R^7$;

$R^6$, $R^7$ are $(C_1-C_6)$-alkyl, sulfamoyl, $N—(C_1-C_4)$-alkylsulfamoyl, $N,N—(C_1-C_4)$-dialkylsulfamoyl, $(C_1-C_6)$-alkoxycarbonyl, $N,N—(C_1-C_4)$-dialkylcarbamoyl, $N—(C_1-C_4)$-alkylcarbamoyl, $N—(C_6-C_{12})$-arylcarbamoyl, $(C_6-C_{12})$-arylcarbamoyl substituted in the aryl radical by $(C_1-C_4)$-alkyl, $(C_1-C_4)$-alkoxy, halogen, $NO_2$, $NH_2$, CN or $CF_3$, carbamoyl, $(C_1-C_6)$-alkylcarbonyl, $(C_6-C_{12})$-arylcarbonyl, $(C_6-C_{12})$-arylcarbonyl substituted in the aryl radical by $(C_1-C_4)$-alkyl, $(C_1-C_4)$-alkoxy, halogen, $NO_2$, $NH_2$, CN or $CF_3$, $(C_1-C_6)$-alkylsulfonyl, $(C_1-C_6)$-alkylsulfinyl, $(C_6-C_{12})$-arylsulfonyl, $(C_6-C_{12})$-arylsulfonyl substituted in the aryl radical by $(C_1-C_4)$-alkyl, $(C_1-C_4)$-alkoxy, halogen, $NO_2$, $NH_2$, CN or $CF_3$, heteroarylcarbonyl or heteroarylsulfonyl or one of the substituents $R^6$, $R^7$ is hydrogen, and their physiologically tolerable salts.

Particularly preferred compounds of the formula I are those in which $R^1$ is —$CH_2$—OH, —$CH_3$, $R^4$, $R^5$ are hydrogen, $R^2$, $R^3$, together with the nitrogen to which they are bonded, are a piperazino group, where this piperazino group is substituted in the 4-position by an N,N-dimethylaminosulfonyl group.

U.S. Pat. No. 5,138,058, WO 94107867, and the scientific literature [e.g. K. Geisen, R. Utz, H. Grötsch, H. J. Lang and H. Nimmesgern, Arzneimittel-Forsch./Drug Res. 44 (II) (1994): 1032–1043] describe a large number of pharmacological actions for the compounds of the formula I. The disclosures of these three documents are specifically incorporated by reference herein. Thus, for example, by treatment of diabetic animals with the pyrimidine derivatives of the formula I a significant improvement in the nerve conduction velocity is achieved. Additionally, in the treatment of diabetic rats with the pyrimidines mentioned, a normalization of the glomerular filtration rate and a decrease in albuminuria is observed. The effects described in the literature make the compounds useful pharmaceuticals for the prophylaxis and treatment of disorders of the diabetic type, in particular for the prophylaxis and treatment of late diabetic damage.

It has now surprisingly been found that the pyrimidine derivatives of the formula I described in the literature mentioned and the patents indicated are able to decrease or to inhibit completely the development of tumors. Thus the compounds mentioned are already able on their own and without addition of other substances to bring about a favorable therapeutic inhibition, in particular of tumor formation.

The present invention also relates to pharmaceutical preparations which, beside nontoxic, inert pharmaceutically suitable excipients, contain one or more active compounds according to the invention or which consist of one or more active compounds according to the invention, and to processes for the production of these preparations.

Nontoxic inert pharmaceutically suitable excipients are understood as meaning pharmaceutically acceptable solid, semisolid or liquid diluents, fillers and formulation auxiliaries of any type, which after mixing with the active compound bring this into a form suitable for administration.

Suitable administration forms of the compounds according to the invention are, for example, tablets, coated tablets, capsules, pills, aqueous solutions, suspensions and emulsions, if appropriate sterile injectable solutions, nonaqueous emulsions, suspensions and solutions, sprays and also preparation forms with protracted release of active compound.

The therapeutically active compounds should be present in the abovementioned pharmaceutical preparations expediently in a concentration of approximately 0.1 to 99.0, preferably of 0.5 to 70.0, percent by weight of the total mixture.

The administration concentrations for solutions and aerosols in the form of spray is in general 0.1 to 20, preferably 0.5–5, percent by weight.

The abovementioned pharmaceutical preparations can also contain further pharmaceutical active compounds in addition to the active compounds according to the invention.

The abovementioned pharmaceutical preparations are prepared in a customary manner according to known methods, e.g. by mixing the active compound(s) with the excipient(s).

The active compounds or the pharmaceutical preparations can be administered orally, parenterally, intraperitoneally and/or rectally.

The compounds of the present invention and their salts can be used for the production of pharmaceutical preparations which contain an effective amount of the active substance together with excipients and which are suitable for enteral and parenteral administration. Tablets or capsules (gelatin capsules) are preferably used which contain the active compound together with diluents or excipients, e.g. lactose, dextrose, cane sugar, mannitol, sorbitol, cellulose, various types of starch and/or glycerol, and lubricants such as silica, talc, stearic acid or its salts, such as magnesium or calcium stearate, and/or polyethylene glycol. Tablets also contain binders such as magnesium carbonate, magnesium aluminum silicate, starch, gelatin, tragacanth, methylcellulose, sodium carboxymethylcellulose and/or polyvinylpyrrolidone and, if required, colorants, flavorings and sweeteners. Injectable solutions are preferably isotonic aqueous solutions or suspensions, which can be sterilized and can contain auxiliaries, such as preservatives, stabilizers, wetting agents and/or emulsifiers, solubilizers, salts for regulating the osmotic pressure and/or buffer substances. The pharmaceutical preparations according to the invention, which if desired can contain further pharmacologically active substances, are prepared, for example, by means of conventional mixing, granulating and pan-coating processes, and contain 0.1% to preferably 80%, preferably approximately 5% to approximately 65%, of the active compound.

Oral administration takes place in pharmaceutically customary preparations, for example in the form of tablets, coated tablets or capsules, which, for example, per daily dose contain 5 to 1000 mg, preferably 20 to 200 mg, of the active compound as a mixture with a customary excipient and/or constituent, it being possible to give individual doses of 5 to 200 mg, preferably once to three times daily.

It may, however, be necessary to deviate from the doses mentioned, namely depending on the nature and the body weight of the subject to be treated, the nature and severity of the disease, the type of preparation and of administration of the pharmaceutical, and the time or interval within which administration takes place. Thus in some cases it may be adequate to manage with less than the abovementioned amount of active compound, while in other cases the abovementioned amount of active compound has to be exceeded. The setting of the optimum dose and type of administration of the active compounds necessary in each case can easily be carried out by any person skilled in the art on the basis of his expert knowledge.

Experimental demonstration of the antitumor action The tumor-prophylactic action of the pyrimidine derivatives of the formula I was tested on rats which had been pretreated with streptozotocin. Streptozotocin is a methylnitrosourea derivative having alkylating properties. It is an oncogenic and cytotoxic substance which was licensed by the US Food and Drug Administration for the treatment of metastatic islet carcinoma of the pancreas. In rats, a single intravenous bolus injection of streptozotocin leads to the acute occurrence of diabetes mellitus and over a longer period of time to the formation of adenomas and adenocarcinomas of the kidney (Lit of Dr. Geisen VII–XII). In this model of streptozotocin-treated rats, chronic treatment with the pyrimidine derivatives according to the invention leads to the almost complete abolition of the development of renal tumors, whereas 80% of the untreated animals show the formation of adenocarcinomas in the kidneys.

EXPERIMENTAL EXAMPLE 24 male rats having a body weight of 210–230 g were administered 60 mg/kg of streptozotocin sulfate intravenously for tumor induction. Six weeks after administration of streptozotocin, 12 of the 24 diabetic animals received a dose of 50 mg/kg of 2-methyl4-(4-N,N-dimethylaminosulfonyl-1-piperazino)pyrimidine orally supplied daily with the drinking water.

After 288 days of treatment, the experiment was ended, 3 animals of the control group and 2 animals of the group treated with 2-methyl-4-(4-N,N-dimethylaminosulfonyl-1-piperazino)pyrimidine dying prematurely. The kidney weight of the control animals was significantly higher than the kidney weight of the animals which received 2-methyl-4-(4-N,N-dimethylaminosulfonyl-1-piperazino)pyrimidine. Only one of ten of the animals treated with 2-methyl-4-(4-N,N-dimethylaminosulfonyl-1-piperazino)pyrimidine had developed a tumor of the size of a lentil in a kidney. In contrast, 7 of the 9 control animals developed pea- to bean-size tumors.

According to the invention, the use of a pyrimidine derivative of the formula I is therefore suitable for the production of a pharmaceutical for the inhibition of tumor growth and for the prevention of tumorigenesis.

The use of a pyrimidine derivative of the formula I for the production of a pharmaceutical for the prevention of oncoses in combination with a therapeutic used in cancer prevention and cancer treatment is preferred.

The use of a pyrimidine derivative of the formula I for the production of a pharmaceutical for the prevention of oncoses in combination with a physical, tumor-therapeutic measure, in particular radiation therapy or hyperthermia therapy, is further preferred.

The use of a pyrimidine derivative of the formula I for the production of a pharmaceutical for the prevention of oncoses in combination with an immunomodulator is likewise preferred.

The use of a pyrimidine derivative of the formula I for the production of a pharmaceutical for the prevention of oncoses in combination with an inhibitor of the cellular sodium-hydrogen exchanger is furthermore preferred.

The use of a pyrimidine derivative of the formula I in combination with other substances which potentiate the action of the pyrimidine derivatives, without themselves having an action directed against tumor formation and tumor growth, for the production of a pharmaceutical for the prevention of oncoses is particularly preferred.

The use of a pyrimidine derivative of the formula I for the production of a pharmaceutical for the prevention of oncoses in combination with pharmacologically tolerable acids or acid-producing nutritive measures is furthermore preferred.

The use of a pyrimidine derivative of the formula I for the production of a pharmaceutical for the prevention of oncoses in combination with modulators of biological pH regulation is furthermore preferred.

The use of a pyrimidine derivative of the formula I for the production of a pharmaceutical for the prevention of oncoses in combination with inhibitors of carboanhydratase is furthermore preferred.

The use of a pyrimidine derivative of the formula I for the production of a pharmaceutical for the prevention of oncoses in combination with an inhibitor of the chloride-bicarbonate exchanger is furthermore preferred.

The use of 2-methyl4-(4-N,N-dimethylaminosulfonyl-1-piperazino)-pyrimidine and of 2-hydroxymethyl4-(4-N,N-dimethylaminosulfonyl-1-piperazino)pyrimidine as a pyrimidine component of a tumor therapeutic is very particularly preferred.

Even on their own without addition of other substances, the pyrimidine derivatives bring about a favorable therapeutic inhibition of tumor growth or of tumor formation.

The relatively low toxic potential of the pyrimidines described here can be combined advantageously with other forms of treatment possible in cancer treatment, and in many cases more toxic, such as, for example,
with chemotherapeutic measures,
with irradiation measures,
with immunomodulators,
with a hyperthermia treatment,
with inhibitors of the cellular sodium-proton exchanger, such as, for example, with amiloride or HOE 642,
with substances which have an inhibitory action on carboanhydratase,
with parallel administration of therapeutically nontoxic and tolerable acids or acid-producing nutritive treatment (such as, for example, the administration of relatively large amounts of glucose/sucrose, e.g. in the form of cola).

The advantage of such a combined treatment can be that the customary more toxic principles of treatment at present (irradiation, chemotherapy, hyperthermia) can be made milder and decreased and/or the antitumor action of a pyrimidine derivative according to the invention can be potentiated.

What is claimed is:

1. A method for the prevention of a carcinomatous disorder, which comprises administering to a host in need of said prevention an effective amount of at least one compound of formula I

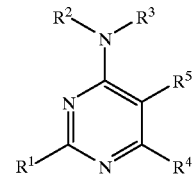

or a physiologically tolerable salt thereof,
in which
$R^1$ is hydrogen, halogen, cyano, nitro, trifluoromethyl, amino, $(C_1-C_6)$-alkyl, $(C_1-C_6)$-hydroxyalkyl, $(C_1-C_6)$-alkoxy, $(C_6-C_{12})$-aryl, $(C_1-C_6)$-alkoxycarbonyl-$(C_1-C_6)$-alkyl, $(C_1-C_6)$-alkyl—S—$(C_1-C_6)$-alkyl, $(C_1-C_6)$-alkyl-SO—$(C_1-C_6)$-alkyl, $(C_1-C_6)$-alkyl—SO$_2$—$(C_1-C_6)$-alkyl, dihydroxy-$(C_1-C_6)$-alkyl, aryl, heteroaryl, heteroaryl-$(C_1-C_6)$-alkyl, aryl-$(C_1-C_6)$-alkyl, $(C_1-C_6)$-alkoxycarbonylaryl, aryl-$(C_1-C_6)$-alkyloxy or heteroaryl-$(C_1-C_6)$-alkyloxy, wherein heteroaryl is pyridyl, furyl, tetrahydrofuryl, thienyl, imidazolyl, pyrazolyl, triazolyl, thiazolyl, oxazolyl, or benzothiazolyl;

where aryl and heteroaryl independently of one another can be unsubstituted or substituted by one or more substituents selected from chlorine, bromine, $(C_1-C_6)$-alkyl, $(C_1-C_6)$-alkoxy, —S—$(C_1-C_6)$-alkyl, —SO—$(C_1-C_6)$-alkyl, —SO$_2$—$(C_1-C_6)$-alkyl, hydroxy-$(C_1-C_6)$-alkyl, and trifluoromethyl, or $R^1$ is 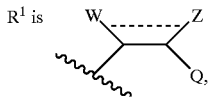

in which the dashed line is an optional bond;

W, Q, Z independently of one another are H, $(C_1-C_6)$-alkyl, trifluoromethyl, phenyl, furyl, triazolyl, thiazolyl, or thienyl, where phenyl, furyl, triazolyl, thiazolyl, thienyl independently of one another can be mono- to trisubstituted by $(C_1-C_6)$-alkyl, $(C_1-C_6)$-alkoxy, trifluoromethyl, or hydroxyl, or $R^1$ is —(C=O)—$R^6$ $R^6$ is H, $(C_1-C_6)$-alkyl, aryl, or heteroaryl wherein heteroaryl is pyridyl, furyl, tetrahydrofuryl, thienyl, imidazolyl, pyrazolyl, triazolyl, thiazolyl, oxazolyl, or benzothiazolyl; where aryl and heteroaryl independently of one another can be unsubstituted or substituted by one to three substituents selected from chlorine, bromine, nitro, trifluoromethyl, $(C_1-C_6)$-alkoxy, —S—$(C_1-C_6)$-alkyl, —SO—$(C_1-C_6)$-alkyl, and —SO$_2$—$(C_1-C_6)$-alkyl, or $R^1$ is 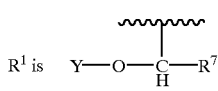

$R^7$ is aryl or heteroaryl
wherein heteroaryl is pyridyl, furyl, thienyl, imidazolyl, pyrazolyl, triazolyl, thiazolyl, oxazolyl, benzothiazolyl, benzofuranyl, benzothienyl, or quinoyl, where aryl and heteroaryl independently of one another can be unsubstituted or substituted by one to three substituents selected from chlorine, bromine, nitro, trifluoromethyl, $(C_1-C_6)$-alkyl, $(C_1-C_6)$-alkoxy, —S—$(C_1-C_6)$-alkyl, —SO—$(C_{1-6})$-alkyl, and —SO$_2$—$(C_1-C_6)$-alkyl;

$R^2$, $R^3$ independently of one another are hydrogen, $(C_{1-6})$-alkyl, $(C_6-C_{12})$-aryl, or $(C_6-C_{12})$-arylalkyl having 1–4 alkyl carbon atoms, where aryl can be unsubstituted or substituted by one to three substituents selected from chlorine, bromine, trifluoromethyl, $(C_1-C_6)$-alkyl, and $(C_1-C_6)$-alkoxy, or $R^2$ and $R^3$, together with the nitrogen to which they are bonded, form the azetidino, pyrrolidino, piperidino, piperazino or morpholino group, where the heterocycles can be unsubstituted or substituted by one or two substituents selected from chlorine, bromine, trifluoromethyl, $(C_1-C_6)$-alkyl, $(C_1-C_6)$-alkoxy, —S—$(C_1-C_6)$-alkyl, —SO—$(C_1-C_6)$-alkyl, —SO$_2$—$(C_1-C_6)$-alkyl, sulfamoyl, N—$(C_1-C_4)$-alkylsulfamoyl, N,N—$(C_1-C_4)$-dialkylsulfamoyl, $(C_1-C_6)$-alkoxycarbonyl, N,N—$(C_1-C_4)$-dialkylcarbamoyl, N—$(C_1-C_4)$-alkylcarbamoyl, N—$(C_6-C_{12})$-arylcarbamoyl, $(C_6-C_{12})$-arylcarbonyl substituted in the aryl radical by $(C_1-C_4)$-alkyl, $(C_1-C_4)$-alkoxy, halogen, NO$_2$, NH$_2$, CN or CF$_3$, $(C_6-C_{12})$-arylcarbonyl substituted in the aryl radical by $(C_1-C_4)$-alkoxy, halogen, NO$_2$, NH$_2$, CN or CF$_3$, $(C_1-C_6)$-alkylsulfonyl, $(C_1-C_6)$-alkylsulfinyl, $(C_6-C_{12})$-arylsulfonyl, $(C_6-C_{12})$-arylsulfonyl substituted in the aryl radical by $(C_1-C_4)$-alkyl, $(C_1-C_4)$-alkoxy, halogen, NO$_2$, NH$_2$, CN or CF$_3$, heteroarylcarbonyl or heteroarylsulfonyl;

$R^4$ and $R^5$ independently of one another are hydrogen, halogen, cyano, nitro, trifluoromethyl, amino, $(C_1-C_6)$-alkyl, $(C_1-C_6)$-hydroxyalkyl, $(C_1-C_6)$-alkoxy, $(C_6-C_{12})$-aryl, naphthyl, or furyl, where $(C_6-C_{12})$-aryl, naphthyl and furyl can be unsubstituted or substituted by one or two substituents selected from chlorine, bromine, trifluoromethyl, $(C_1-C_6)$-alkyl, $(C_1-C_6)$-alkoxy, —S—$(C_1-C_6)$-alkyl, —SO—$(C_1-C_6)$-alkyl, —SO$_2$—$(C_1-C_6)$-alkyl, and hydroxyl.

2. A method as claimed in claim 1, wherein the radicals $R^1$ to $R^7$ have the following meaning $R^1$ is cyano, trifluoromethyl, $(C_1-C_6)$-alkyl, $(C_1-C_6)$-hydroxyalkyl, $(C_1-C_6)$-alkoxy or $(C_6-C_{12})$-aryl;

$R^4$ and $R^5$ independently of one another are hydrogen, halogen or trifluoromethyl;

$R^2$, $R^3$ independently of one another are hydrogen, $(C_1-C_6)$-alkyl, $(C_6-C_{12})$-aryl or $(C_6-C_{12})$-arylalkyl having 1–4 alkyl carbon atoms, or $R^2$ and $R^3$, together with the nitrogen to which they are bonded, form the azetidino, pyrrolidino, piperidino, piperazino or morpholino group, or an azetidino, pyrrolidino, piperidino, piperazino or morpholino group substituted by identical or different groups $R^6$ and $R^7$;

$R^6$, $R^7$ are $(C_1-C_6)$-alkyl, sulfamoyl, N—$(C_1-C_4)$-alkylsulfamoyl, N,N—$(C_1-C_4)$-dialkylsulfamoyl, $(C_1-C_6)$-alkoxycarbonyl, N,N—$(C_1-C_4)$-dialkylcarbamoyl, N—$(C_1-C_4)$-alkylcarbamoyl, N—$(C_6-C_{12})$-arylcarbamoyl, $(C_6-C_{12})$-arylcarbamoyl substituted in the aryl radical by $(C_1-C_4)$-alkyl, $(C_1-C_4)$-alkoxy, halogen, NO$_2$, NH$_2$, CN or CF$_3$, carbamoyl, $(C_1-C_6)$-alkylcarbonyl, $(C_6-C_{12})$-arylcarbonyl, $(C_6-C_{12})$-arylcarbonyl substituted in the aryl radical by $(C_1-C_4)$-alkyl, $(C_1-C_4)$-alkoxy, halogen, NO$_2$, NH$_2$, CN or CF$_3$, $(C_1-C_6)$-alkylsulfonyl, $(C_1-C_6)$-alkylsulfinyl, $(C_6-C_{12})$-arylsulfonyl, $(C_6-C_{12})$-arylsulfonyl, substituted in the aryl radical by $(C_1-C_4)$-alkyl, $(C_1-C_4)$-alkoxy, halogen, NO$_2$, NH$_2$, CN or CF$_3$, heteroarylcarbonyl or heteroarylsulfonyl or one of the substituents $R^6$, $R^7$ is hydrogen.

3. A method as claimed in claim 1, wherein the radicals $R^1$ to $R^7$ have the following meaning $R^1$ is —CH$_2$—OH, or —CH$_3$, $R^4$, $R^5$ are hydrogen, $R^2$, $R^3$, together with the nitrogen to which they are bonded, are a piperazino group, where this piperazino group is substituted in the 4-position by an N,N-dimethylaminosulfonyl group.

4. A method of claim 1, wherein the compound of the formula I is 2-methyl-4-(4-N,N-dimethylaminosulfonyl-1-piperazino)pyrimidine or 2-hydroxymethyl-4-(4-N,N-dimethylamino-sulfonyl-1-piperazino)pyrimidine.

5. A method as claimed in claim 1, wherein the carcinomatous disorder is a tumor.

* * * * *

UNITED STATES PATENT AND TRADEMARK OFFICE
CERTIFICATE OF CORRECTION

PATENT NO. : 6,156,755
DATED : December 5, 2000
INVENTOR(S) : Karl Geisen

It is certified that error appears in the above-identified patent and that said Letters Patent is hereby corrected as shown below:

<u>Title page</u>,
Item [73] Assignee, "Frankfurt" should read -- Frankfurt am Main --.

<u>Column 7</u>,
Line 50, "–SO–($C_{1-6}$)-alkyl" should read -- –SO–($C_1$–$C_6$)-alkyl --.
Lien 53 "($C_{1-6}$)-alkyl" should read -- ($C_1$–$C_6$)-alkyl --.

Signed and Sealed this

Eleventh Day of June, 2002

Attest:

JAMES E. ROGAN
Attesting Officer    Director of the United States Patent and Trademark Office